US010026195B2

(12) United States Patent
Summerfield

(10) Patent No.: US 10,026,195 B2
(45) Date of Patent: Jul. 17, 2018

(54) IMAGE RECOGNITION BASE ABLATION PATTERN POSITION RECALL

(71) Applicant: Elemental Scientific Lasers, LLC, Omaha, NE (US)

(72) Inventor: Leif Christian Summerfield, Bozeman, MT (US)

(73) Assignee: ELEMENTAL SCIENTIFIC LASERS, LLC, Omaha, NE (US)

(*) Notice: Subject to any disclaimer, the term of this patent is extended or adjusted under 35 U.S.C. 154(b) by 132 days.

(21) Appl. No.: 14/211,976

(22) Filed: Mar. 14, 2014

(65) Prior Publication Data

US 2014/0288693 A1 Sep. 25, 2014

Related U.S. Application Data

(60) Provisional application No. 61/792,016, filed on Mar. 15, 2013.

(51) Int. Cl.
*G06T 7/73* (2017.01)
*G01N 1/04* (2006.01)

(52) U.S. Cl.
CPC .......... *G06T 7/74* (2017.01); *G01N 2001/045* (2013.01); *G05B 2219/50057* (2013.01); *G06T 2207/30108* (2013.01)

(58) Field of Classification Search
CPC .... B23K 26/032; B23K 26/08; B23K 26/381; G06T 7/0044; G06T 2207/30108; G01N 2001/045; G05B 2219/50057
(Continued)

(56) References Cited

U.S. PATENT DOCUMENTS 5,523,543 A * 6/1996 Hunter, Jr. ............ G01J 1/4257
219/121.62
5,844,149 A 12/1998 Akiyoshi et al.
(Continued)

FOREIGN PATENT DOCUMENTS

CN 1667359 A 9/2005
CN 1693938 A 11/2005
(Continued)

OTHER PUBLICATIONS

A new approach to single shot laser ablation analysis and its application to in situ Pb/U geochronology, Published on Jul. 30, 2009 (pp. 1355-1363) By: J. M. Cottle, M. S. A. Horstwoodb and R. R. Parrish.*

(Continued)

*Primary Examiner* — Robert E Fennema
*Assistant Examiner* — Jigneshkumar C Patel
(74) *Attorney, Agent, or Firm* — Kevin E. West; Advent, LLP

(57) ABSTRACT

Embodiments of the present invention exemplarily described herein relate generally to saving XYZ stage coordinates for intended laser locations as well as a kernel image of an ablation pattern placed during a scan placement process, and comparing the kernel image to a current image of the current field of view of a camera/microscope that includes the location a laser would be fired at. This comparison is used during an experimental run to correct for any built up error. More particularly, embodiments of the present invention relate to apparatuses and methods for software based image recognition to correct errors in open looped systems for positioning a sample relative to a laser in analysis systems for zircon crystal grain dating.

7 Claims, 4 Drawing Sheets

(58) Field of Classification Search
USPC .......................................................... 700/166
See application file for complete search history.

(56) References Cited

U.S. PATENT DOCUMENTS

| | | | |
|---|---|---|---|
| 8,779,326 | B2 | 7/2014 | Rumsby |
| 2006/0249480 | A1 | 11/2006 | Boyle |
| 2007/0012665 | A1 | 1/2007 | Nelson et al. |
| 2007/0050165 | A1* | 3/2007 | Gray ........................ A61B 3/00 702/108 |
| 2009/0073586 | A1 | 3/2009 | Fry et al. |
| 2009/0255911 | A1 | 10/2009 | Krishnaswami et al. |
| 2009/0273782 | A1 | 11/2009 | Yoo et al. |
| 2009/0314751 | A1* | 12/2009 | Manens .......... H01L 31/022425 219/121.69 |
| 2011/0198496 | A1 | 8/2011 | Ikegami et al. |
| 2012/0099103 | A1* | 4/2012 | Hahn .................... G01N 21/718 356/316 |
| 2013/0158698 | A1* | 6/2013 | Jeong ................. H01L 31/0322 700/121 |

FOREIGN PATENT DOCUMENTS

| | | |
|---|---|---|
| CN | 101584051 A | 11/2009 |
| CN | 101990480 A | 3/2011 |
| CN | 102194642 A | 9/2011 |

OTHER PUBLICATIONS

International Preliminary Report on Patentability for Application No. PCT/US2014/028241; dated Sep. 15, 2015; 4 pgs.
International Search Report and Written Opinion of Internation Application No. PCT/US2014/028241; dated Jul. 17, 2014; 8 pgs.
Wanner et al .. Laser ablation inductively coupled plasma mass spectrometry 1-5 (LA-ICP-MS) for spatially resolved trace element determination of solids using an autofocus system, Spectrochimica Acta Part B: Atomic Spectroscopy, 1999, vol. 54, No. 2, pp. 289-298.
Office Action (with English Translation), Chinese, Application No. 201480015608.X, dated Dec. 20, 2016, 14 pages.
Barrett, et al., "Digital Tracking and Control of Retinal Images," Optical Engineering, Soc. of Photo-Optical Instrumentation Engineers, Bellingham, vol. 33, No. 1, Jan. 1, 1994 (Jan. 1, 1994), pp. 150-159.
Doignon, et al. "Autonomous 3-d positioning of surgical instruments in robotized laparoscopic surgery using visual servoing", IEEE Transactions on Robotics and Automation, IEEE Inc, New York, US, vol. 19, No. 5, Oct. 1, 2003 (Oct. 1, 2003), pp. 842-853.
Search Report, Supplementary European, Application No. EP 14 76 2234, dated Sep. 28, 2016, 10 pages.
Office Action dated Mar. 7, 2018 for Taiwan Appln. No. 103109576.

* cited by examiner

IMAGE RECOGNITION BASE ABLATION PATTERN POSITION RECALL

RELATED APPLICATIONS

This application claims benefit of U.S. provisional patent application No. 61/792,016 filed on 15 Mar. 2013, the disclosure of which is incorporated by reference.

BACKGROUND OF THE INVENTION

Analysis systems, such as mass spectrometry (MS) systems, optical emission spectrometry (OES) systems and the like, can be used to analyze the composition of a target material, for example a solid crystal. Often, a sample of the target is provided to analysis systems of this type in the form of an aerosol. The aerosol is typically produced by arranging the target material in a sample chamber, introducing a flow of a carrier gas within the sample chamber, and ejecting a portion of the target in the form of particles. The ejecting may be done for example by laser ablating a portion of the target with one or more laser pulses, from a laser, to generate a plume containing particles and/or vapor ejected or otherwise generated from the target suspended within the carrier gas. Thereafter, the ejected particles are typically entrained by the flowing carrier gas and transported to an analysis system via a sample transport conduit. These analysis systems perform applications including Laser ablation Inductively Coupled Plasma Mass Spectrometry (LA-ICP-MS) and Laser ablation Inductively Coupled Plasma Optical Emission Spectrometry (LA-ICP-OES)

Analytical laser ablation applications require repeated movement of an XY, or XYZ, positioning system during experimental runs performed subsequently to a scan placement process in which movements to be repeated during the experimental run are set. One exemplary use of analytical laser ablation systems is for zircon crystal grain dating. Zircon crystals incorporate uranium and thorium atoms into the crystalline structure, and strongly reject lead during the formation of the crystal. Therefore, any lead present in a zircon crystal is assumed to be from radioactive decay. Therefore, if the composition of a zircon crystal is determined the age of the crystal can be determined by calculating the amount of time it would take to produce the ratio of uranium to lead in the crystal through radioactive decay.

Zircon crystal grains used for dating frequently have very small dimensions, for example a single grain may range in size from 20 um across to 200 um across points in an outline of the crystal grain. Within the crystals invisible structures may exist that can be imaged using an SEM, XRF or other similar tool. These invisible structures may cause areas of a crystal grain to be not ideal for certain analytical laser ablation applications. For these reasons a desired target on a zircon crystal grain for zircon crystal dating, and similar applications, may be a very small and thus these applications require very high precision for ablating a surface of a crystal grain, and therefore require high precision stage movement.

During a typical zircon crystal grain aging application an exemplary sample slide may be prepared containing approximately 20-200+ grains in an approximately 50 mm by 50 mm area. The grains may be placed on the slide automatically or by a user. The grains may be placed in a random arrangement or in an orderly pattern, such as in rows and columns. Further, the grains may be placed according to sets of crystal grains to be analyzed together. After placement the grains may be machined to have flat surfaces substantially on the same plane as the other grains on the sample slide.

After the sample slide is prepared it is loaded into a sample chamber of an analytical laser ablation device and a scan placement process is performed. An operator places a pattern scan, also referred to as an overlay, on the sample slide. This may be done with using software to perform a virtual overlay of pattern shapes. During this process the locations of a series of scans or holes to be fired upon by the laser are set in precise positions, for example at specific locations on the machined faces of individual crystal grains. These set positions are referred to as intended laser locations. Once the scan placement process is complete an experimental run occurs where a motion control system executes a series of movements determined by the scan placement process to ablate each crystal grain at the intended laser locations at a desired time and sequence.

As part of the experimental setup a reference material blank is usually placed in the sample chamber of a laser ablation apparatus, such as off to one side of the main experiment area. The reference blank has a known composition. The system may be set to analyze sets of zircon crystals grains and between sets of zircon crystal grains the system will then be programmed to sample the reference blank material. In this way, analytical drifts measured at an ICP-MS for example can be corrected for given the reference's known and repeatable concentrations of material.

During the scan placement process a list of intended laser locations are saved as XY, or XYZ, stage coordinates. During the experimental run, for each intended laser location the sample is moved relative to the laser by the motion control system according to the saved coordinate position.

During an experimental run a motion control system will move the sample slide relative to the laser for each incrementally setup intended laser location on a zircon crystal grain in a set in the sample and then to the reference blank, then back to the next set of crystal grains. With each large movement either between crystal grains with intended laser locations, or to the reference blank a bi-directional repeatability error may appear to shift the sample slide relative to the laser beam's position. A large 30 mm move can incur a built up bi-directional repeatabilty or accuracy error that will shift the laser focus position off of the intended laser position on a crystal grain. The precision with which the ablation pattern was placed relative to the sample will be reduced by the time the laser is to be fired if a repeatability error accumulates. In some cases the laser will fire in an unintended location, including missing the crystal grain with an intended laser location thereon altogether. This is undesirable since a laser firing at an unintended location will skew or ruin the data for that experiment pass.

Due to the large number of zircon crystals often sampled during the same experimental run, such as 20 to 200+ crystal grains, it is undesirably time consuming for an operator to monitor the equipment and correct for poor system level accuracy of the laser beam on the sample during the experimental run.

Conventional techniques for XYZ positioning systems include motion control topologies, such as open loop and closed loop. Open loop designs may be stepper motor based, and move the stage via linear type motors or lead-screw drive type mechanisms a precise amount, for example a fraction of the actual full step range. Each step can be on the order of 1-2 um of XY movement, with microstepping adding a divide by 2, 4, 8, 16 or 32 microsteps per full step. In this way it is possible to attempt positioning at a very high resolution, only limited by the mechanical coupling of the stage mechanism. Closed loop adds to this a feedback mechanism and a controller topology that attempts to reduce requested position-actual position error until the error is zero or very small. These solutions have the disadvantage of requiring costlier stages and controllers and are complicated to implement.

BRIEF SUMMARY OF THE INVENTION

Embodiments of the present invention exemplarily described herein relate generally to saving XYZ stage coordinates for intended laser locations as well as a kernel image of an ablation pattern placed during a scan placement process, and comparing the kernel image to a current image of the current field of view of a camera/microscope that includes the location a laser would be fired at. This comparison is used during an experimental run to correct for any built up error. More particularly, embodiments of the present invention relate to apparatuses and methods for software based image recognition to correct errors in open looped systems for positioning a sample relative to a laser in analysis systems for zircon crystal grain dating.

DETAILED DESCRIPTION OF THE INVENTION

Figure 1:
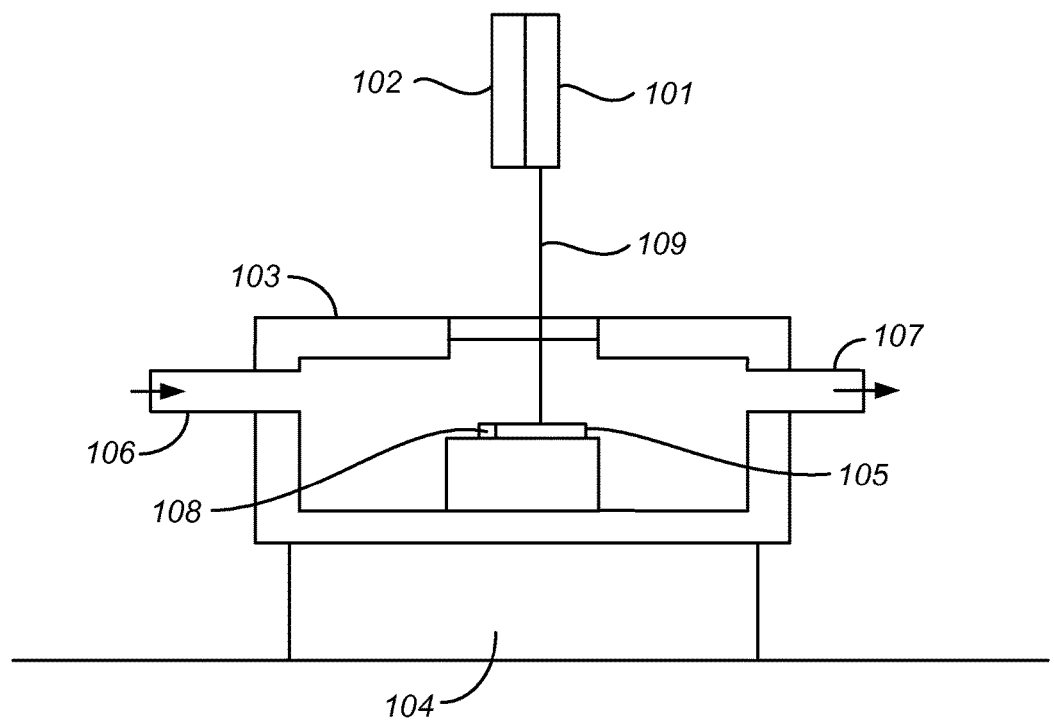
FIG. 1 is a cross sectional view of a laser ablation apparatus.

The following description of the invention will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

FIG. 1 illustrates a cross sectional view of a laser ablation apparatus 100. Laser ablation apparatus 100 includes a laser 101, a camera/microscope 102 fixed relative to the laser 101, a sample chamber 103, and a motion control system 104 which controls movements of the sample chamber 103 relative to the laser 101 and camera/microscope 102. To begin analysis a sample slide 105 is placed within the sample chamber 103. The sample chamber includes an inlet conduit 106 to allow in a flow of carrier gas and a sample transport conduit 107 to allow the exit of carrier gas. Within the sample chamber 103 is a reference blank 108 which may be separate or integral with the sample slide 105.

Figure 2:
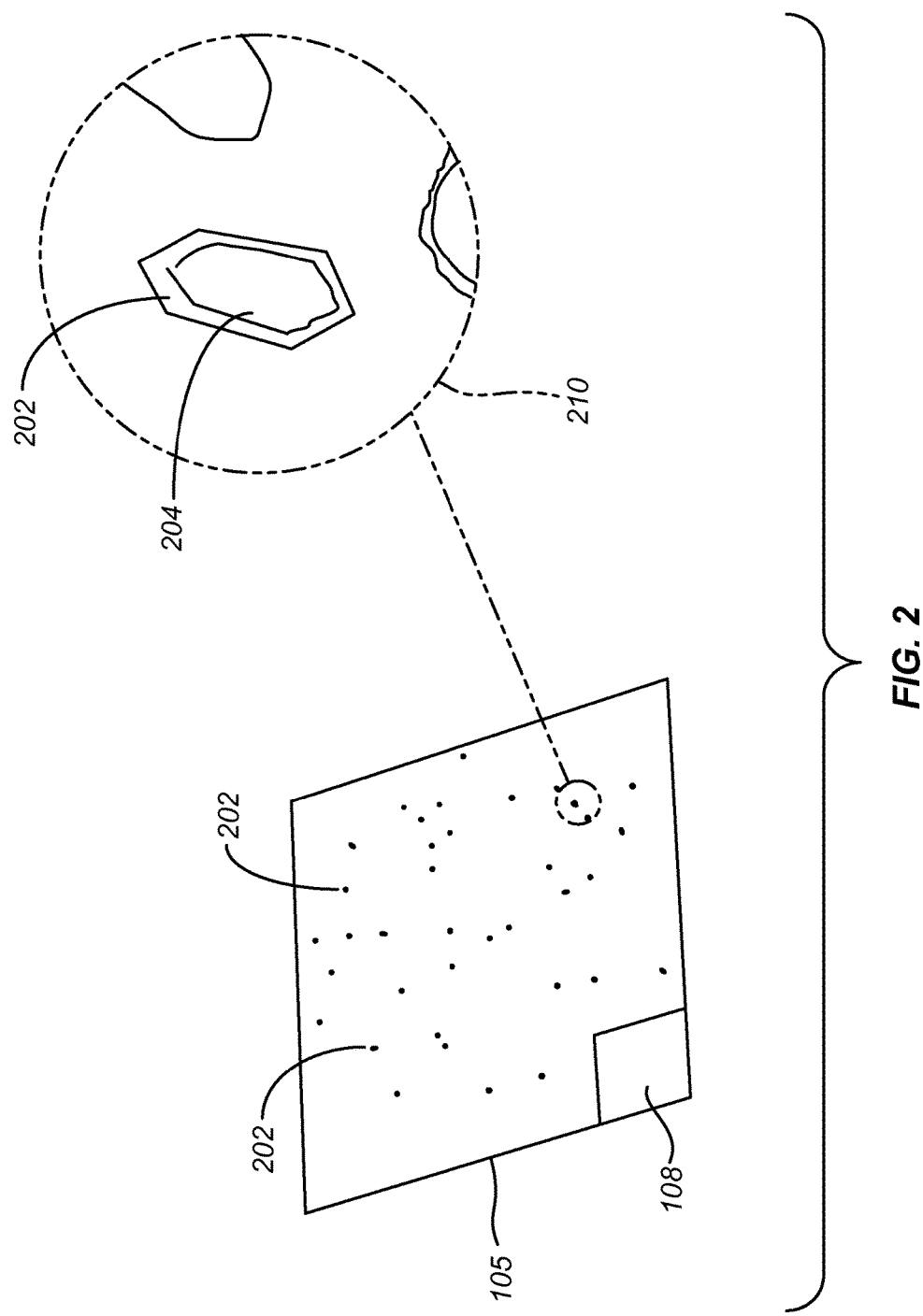
FIG. 2 illustrates a sample slide containing zircon crystal grains.

FIG. 2 illustrates a sample slide 105 and a zoomed in view 201 of a portion of the surface of the slide. On the surface of the sample slide 105 there is a plurality of zircon crystal grains 202. In embodiments each crystal is machined to have a flat surface 204.

Embodiments of the invention include software based image recognition to correct errors that tend to shift the sample relative to the laser beams during an experimental run. In embodiments, this is done by precisely moving a stage of a motion control system to the intended laser location of an ablation pattern set during a scan placement process. This precise movement is accomplished by comparing images saved during the scan placement process as kernel image with current position images of the camera/microscope field of view and calculating corrective moves.

In embodiments the xyz position in combination with a kernel image will ensure the laser fires precisely at the intended laser locations that were set during the scan placement process by correcting for any movement error incurred when returning to an intended laser position that was set during the scan placement process. In embodiments movement error is less than half the field of view of the camera/microscope, for example 350 um, ensuring that the intended laser location is close enough to appear in the field of view of the camera/microscope view during the experimental run. This current camera/microscope view is then used to compare against the saved kernel image location, and an XY, or XYZ, offset move can be applied to correct for the error.

Figure 3:
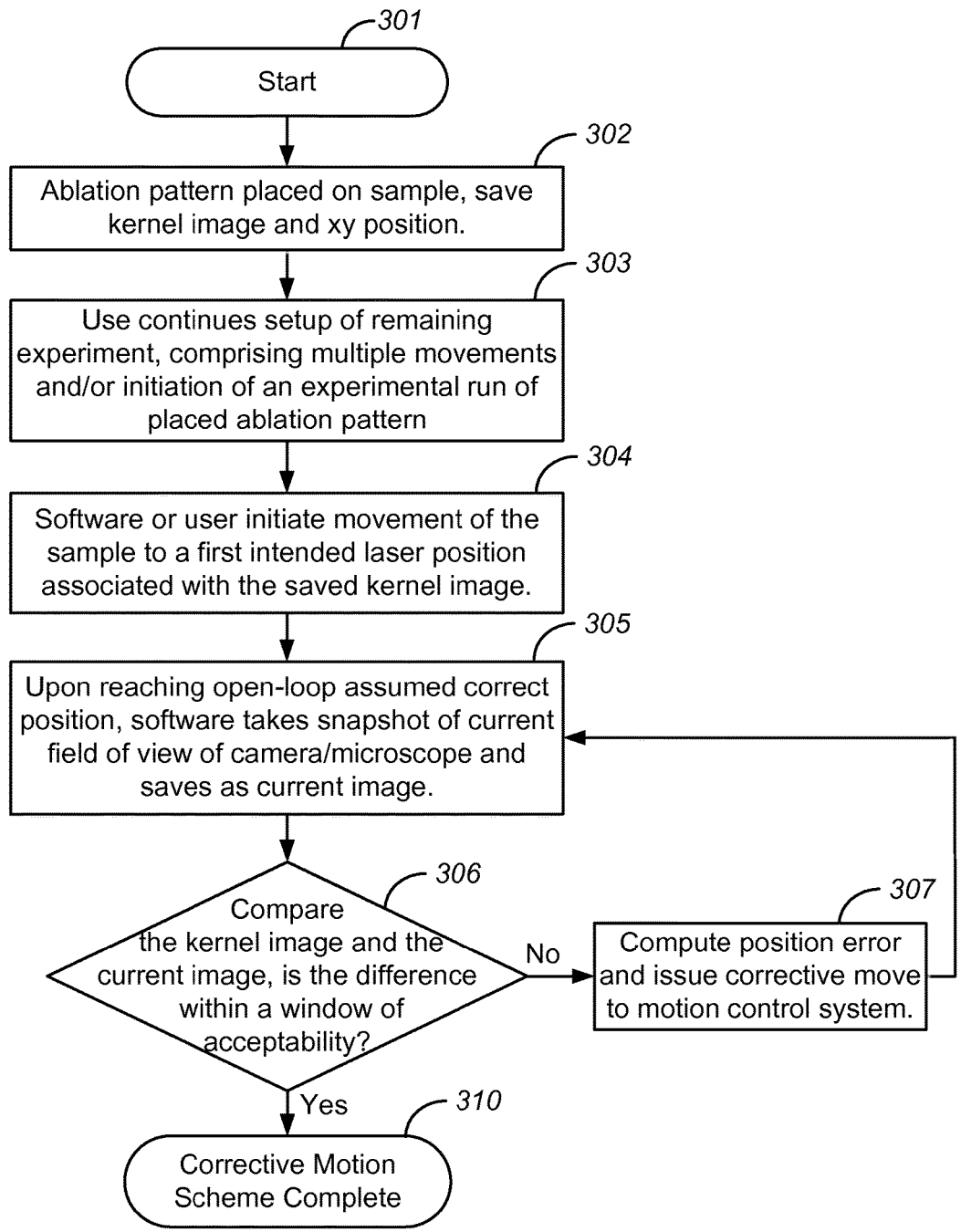
FIG. 3 is a flow chart diagram.
Figure 4A:
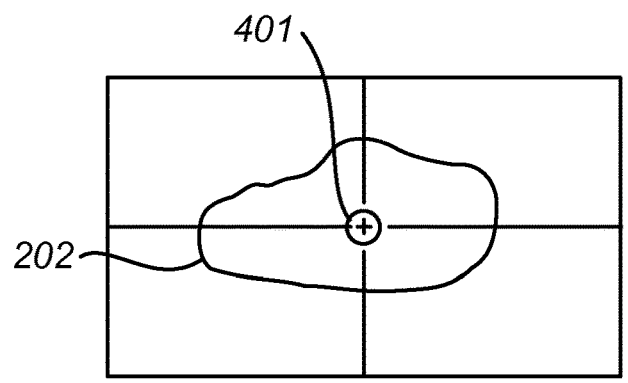
FIGS. 4a-c illustrate the field of view of a camera/microscope during the scan placement and experimental run steps.

FIG. 3 is a flow chart diagram of an embodiment. In the embodiment, the process begins 301 and an ablation pattern is placed onto a sample in a first step 302, for example using software to perform a virtual overlay of pattern shapes. The virtual overlay software using the field of view of the camera/microscope 102 allows a user to view a portion of the sample slide containing a crystal grain 202 and set an intended laser position for a location on a crystal grain. The virtual overlay software further allows a user to set the intended laser positions on a plurality of crystal grains 202 on the sample slide 105 forming an ablation pattern. An embodiment of setting an intended laser location on a crystal grain is illustrated in FIG. 4A showing a field of view of the camera/microscope 102 with crosshairs and a spot representing an intended laser location 401 for a laser to be fired onto a zircon crystal grain 202 located in the field of view. During this step of placing the ablation pattern information about the ablation pattern is saved. In embodiments this information includes XY, or XYZ, positions. In embodiments firing information and movement properties are saved. In embodiments an image of a camera/microscope field of view at the time the intended laser position of the ablation pattern was placed or moved, is saved as the "kernel" image to be used to position the laser to the intended laser positions during an experimental run. In embodiments further saved information includes lighting levels, zoom level and/or camera properties used when capturing the image, which will ensure that video conditions can be fully reproduced during a re-centering step.

Figure 4B:
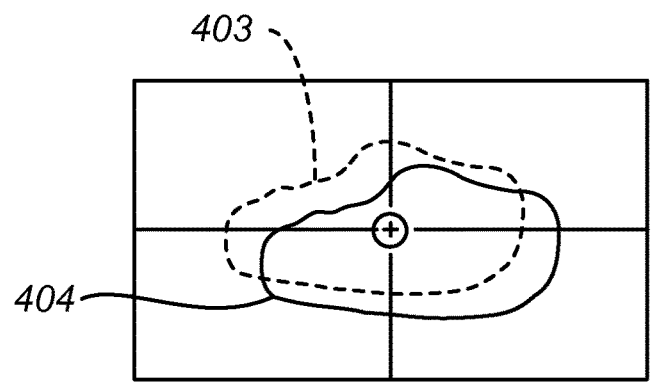

In embodiments, after a kernel imaged is saved a user continues setup of the remaining experiment 303, comprising multiple movements and/or initiation of an experimental scan of the placed pattern(s). Once the experimental run is initiated the next step 304 is for software or a user to initiate movement of the sample to a first intended laser position. Upon reaching the open-loop assumed correct position of the intended laser position a snapshot of the field of view of the camera/microscope is taken 305 corresponding to the current position of the sample relative to the camera. An embodiment of this step is illustrated in FIG. 4b showing the kernel image 403, represented by a dotted outline of crystal grain, corresponding to the intended laser position and a current image 404 of the current field of view of the camera/microscope. As is shown in FIG. 4b the kernel image 403 is not aligned with the current image 404, represented by a full line outline of the same crystal grain present in the kernel image 403, due to some positioning repeatability error.

During a comparing step 306 the difference of the intended laser location and the current laser location is determined by comparing the kernel image and the current image of the current field of view of the camera/microscope. If the difference is determined to be within a window of acceptability, the correct motion scheme is complete 310; if the difference is determined to not be within a window of acceptability, a computing step 307 is executed wherein a position error is computed and a set of corrective moves are issued to and executed by the motion control system 104 which moves the sample relative to the camera/microscope and laser. In embodiments this step is done with image recognition algorithms to calculate the difference between the kernel image and the current image of the current field of view of the camera/microscope. In embodiments the window of acceptability may be predefined, computed by software, or set by an operator. In embodiments the corrective move can be a series of moves until the position error is within a window of acceptability.

Once the stage is repositioned due to corrective moves the step of taking a snapshot of the current position 305 is repeated as is the comparing step 306 in which the difference between the original position from the kernel image and a new current position are compared.

Figure 4C:
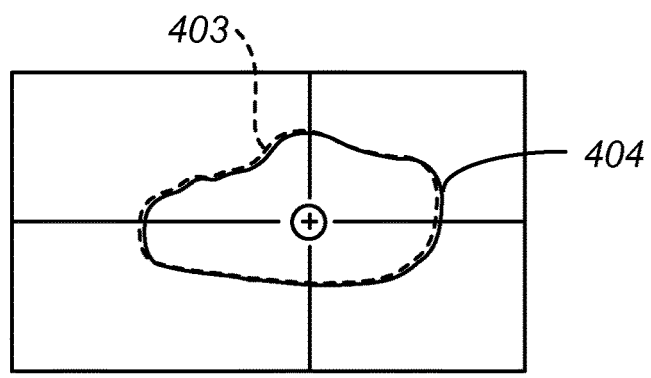

Any time in the process when during the comparing step 306 the difference between the kernel image 403 and the current image 404 of the current field of view of the camera/microscope is within the window of acceptability, as is illustrated in FIG. 4c, the corrective motion scheme is complete 310 and the laser is fired at the intended laser position on the crystal grain. This causes a sample of the crystal grain to be suspended in a carrier gas and analyzed in a spectrometry instrument allowing the composition of the crystal grain to be determined for such application as zircon crystal grain dating.

The primary advantage of this invention is to apply a corrective motion scheme to allow for extremely high precision of laser placement greatly improving the specifications of the same open-loop XYZ stage control and motion system, without adding any system level hardware additions/costs.

In embodiments during which an experiment is run, XY motion control system 104 will move the sample slide 105 relative to the camera/microscope 102 and laser 101 to each incrementally setup intended laser location 401 on a zircon crystal grain 202 in a set of zircon crystal grains, then to the reference blank 108, then back to the next set of zircon crystal grains. In some examples a set of zircon crystal grains could include only 1 grain while in others a set could include 2 or more grains. With each movement either between intended targets on a zircon crystal grains or to the reference blank a bi-directional repeatability error may appear to shift the sample relative to the laser beam 109 position. To correct this bi-directional repeatability error, the corrective motion scheme disclosed above is used to ensure that the laser fires at the intended laser position set during the scan placement process.

The following clauses describe aspects of various examples of methods relating to positioning a laser relative to a crystal grain on a sample.

1. A method for positioning a laser on a crystal grain on a sample on a support surface during a laser ablation procedure comprising: setting an ablation pattern for a sample during a scan placement process comprising; positioning the sample relative to a laser to multiple intended laser positions on the sample with a motion control system, saving position coordinates for each intended laser position, and saving a kernel image for at least one said intended laser positions; and initiating an experiment comprising; positioning the laser relative to the sample to a current position based on the saved coordinates of a chosen one of the intended laser positions with a saved kernel image, comparing a current image of the current position with the saved kernel image for the intended laser, determining a position error based on the comparison, if the position error is not within a window of acceptability, then applying an offset movement of the laser relative to the sample with the motion control system based on the position error to correct for the position error and repeat the comparing and determining steps, and if the position error is within the window of acceptability, then fire a laser beam upon the intended laser position.

2. The method of clause 1, wherein the motion control system is an open-loop system; and wherein the current position is an open-loop assumed correct position.

3. The method of clause 1 or 2, wherein the kernel image and the current image are taken with a camera that is fixed relative to the laser.

4. The method of clause 1, 2 of 3, wherein the step of positioning the laser relative to the sample to current position occurs after sampling a reference blank.

5. The method clause 1, 2, 3, or 4, wherein the step of saving a kernel image for at least one said intended laser positions further includes saving at least one of lighting levels, zoom levels, or camera properties used when capturing the kernel image.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method for positioning a laser on a sample during a laser ablation procedure comprising:
    setting an ablation pattern including multiple intended laser ablation locations for a sample during a scan placement process comprising:
        positioning the sample relative to a laser ablation location to said multiple intended laser ablation locations on the sample with a motion control system;
        saving position coordinates for each of said multiple intended laser ablation locations, and;
        saving a kernel image of the sample at each of said multiple intended laser ablation locations; and
    for all the multiple intended laser ablation locations:
        positioning the laser ablation location relative to the sample to a current position based on the saved coordinates of a chosen one of the multiple intended laser ablation locations with a saved kernel image;
        comparing a current image of the sample at the current position with the saved kernel image of the sample for the chosen intended laser ablation location;
        determining a position error based on the comparison;
        if the position error is not within a window of acceptability, then applying an offset movement of the laser ablation location relative to the sample with the motion control system based on the position error to correct for the position error and repeat the comparing and determining steps; and if the position error is within the window of acceptability, then fire a laser beam upon the sample at the laser ablation location.

2. The method of claim 1, wherein the motion control system is an open-loop system; and wherein, in said positioning the laser ablation location relative to the sample to a current position, the current position is an open-loop assumed correct position.

3. The method of claim 1, wherein the kernel image and the current image are taken with a camera that is fixed relative to the laser ablation location.

4. The method of claim 1, wherein the step of positioning the laser ablation location relative to the sample to a current position occurs after sampling a reference blank.

5. The method of claim 1, wherein the step of saving a kernel image for each of said multiple intended laser ablation locations further includes saving at least one of lighting levels, zoom levels, or camera properties used when capturing the kernel image.

6. The method of claim 1, including flowing a carrier gas over the sample, wherein said laser beam causes material of the sample to be suspended in the carrier gas, and analyzing the material suspended in the carrier gas.

7. The method of claim 6, wherein the sample comprises zircon.

* * * * *